United States Patent
Schwank et al.

(10) Patent No.: US 9,550,106 B1
(45) Date of Patent: Jan. 24, 2017

(54) IMPACT ENERGY ABSORBING MOUTH GUARD

(71) Applicant: Akervall Technologies, Inc., Saline, MI (US)

(72) Inventors: Johann Walter Schwank, Ann Arbor, MI (US); Jan Anders Akervall, Ann Arbor, MI (US); Valarie Thomas, Ann Arbor, MI (US); Timothy Huang, Ann Arbor, MI (US)

(73) Assignee: Akervall Technologies, Inc., Saline, MI (US)

( * ) Notice: Subject to any disclaimer, the term of this patent is extended or adjusted under 35 U.S.C. 154(b) by 0 days.

(21) Appl. No.: 15/179,015

(22) Filed: Jun. 10, 2016

(51) Int. Cl.
  *A63B 71/08* (2006.01)
  *A61F 5/56* (2006.01)
  *A61M 16/04* (2006.01)

(52) U.S. Cl.
  CPC .............. *A63B 71/085* (2013.01); *A61F 5/56* (2013.01); *A61F 5/566* (2013.01); *A61M 16/049* (2014.02)

(58) Field of Classification Search
  CPC ....................... A61M 16/049; A61B 1/267
  See application file for complete search history.

(56) References Cited

U.S. PATENT DOCUMENTS

| | | | |
|---|---|---|---|
| 3,112,744 A * | 12/1963 | Grossberg | 128/862 |
| 4,718,662 A | 1/1988 | North | |
| 4,955,393 A | 9/1990 | Adell | |
| 5,051,476 A | 9/1991 | Uji et al. | |
| 5,082,007 A | 1/1992 | Adell | |
| 5,165,423 A | 11/1992 | Fowler et al. | |
| 5,293,880 A | 3/1994 | Levitt | |
| 5,313,960 A | 5/1994 | Tomasi | |
| 5,692,523 A | 12/1997 | Croll et al. | |
| 6,036,487 A | 3/2000 | Westerman | |
| 6,080,923 A | 6/2000 | Austin | |
| 6,109,266 A | 8/2000 | Turchetti | |
| 6,295,988 B1 | 10/2001 | Sue | |
| 7,404,403 B2 | 7/2008 | Farrell | |
| 2004/0112389 A1 | 6/2004 | Abraham | |
| 2005/0034733 A1 | 2/2005 | Liddle et al. | |
| 2007/0084472 A1 | 4/2007 | Berghash | |
| 2007/0148612 A1* | 6/2007 | Massad | 433/37 |
| 2007/0151568 A1 | 7/2007 | Maurello | |
| 2008/0289639 A1 | 11/2008 | Bancroft | |
| 2009/0038624 A1* | 2/2009 | Akervall et al. | 128/861 |
| 2009/0114232 A1 | 5/2009 | Landi et al. | |
| 2009/0117514 A1* | 5/2009 | Massad | 433/39 |
| 2009/0223526 A1 | 9/2009 | Berghash et al. | |
| 2010/0051038 A1 | 3/2010 | Quigless | |
| 2012/0325225 A1* | 12/2012 | Small | 128/862 |

FOREIGN PATENT DOCUMENTS

| | | |
|---|---|---|
| JP | 08206272 A | 8/1996 |
| JP | 2005342133 A | 12/2005 |

* cited by examiner

*Primary Examiner* — Tarla Patel
(74) *Attorney, Agent, or Firm* — Marshall & Melhorn, LLC (57) ABSTRACT

An energy absorbing mouth guard is provided with several sets of open spaces. The sets are arranged in the guard at preferred locations. At least some of the sets have arrays of open spaces, where the arrays are arranged in a triangular pattern. Each array in the triangular pattern has three open spaces.

20 Claims, 6 Drawing Sheets

IMPACT ENERGY ABSORBING MOUTH GUARD

FIELD OF THE INVENTION

The present invention relates generally to a novel type of impact energy absorbing mouth guard intended to protect the dentitions of people engaged in various sports, dentistry, hospital or military activities.

BACKGROUND OF THE INVENTION

Most over-the-counter boil-and-bite type mouth guards do not provide adequate dental protection as evidenced by the fact that there are more than one million annual orofacial injuries in sports despite the use of mouth guards.

The American Dental Association (ADA) estimates that the lifetime costs for treatment of serious dental injuries are $15,000-$20,000 per tooth, which translates to a total annual cost for dental injuries of half a billion dollars just in the USA. In many cases, the long term consequences of dental injuries are the onset of periodontal or other dental disease, frequently ending up with dental implants.

Low-cost over-the-counter mouth guards suffer from poor fit and are so uncomfortable that athletes tend to remove them intermittently during sports activities. The frequent handling of saliva-coated mouth guards transmits pathogens from dirty hands and fingers to the mouth guards.

Dentist-made custom mouth guards made from acrylic resins require time consuming and very costly laboratory production and fitting procedures. However, these professional-grade mouth guards still are uncomfortable and hinder breathing and talking.

Depending on the type of sports, impacts in the orofacial area can have a wide range of peak forces that are reached over relatively short time periods. Furthermore, the area of impact can vary widely, depending on whether the impact is caused by an object such as a hockey puck or stick, or caused by a crash landing on the chin or cheek where a larger area will be impacted but a lower overall peak forces.

In view of the disadvantages with the prior art mouth guards, it would be beneficial for a mouth guard to provide superior impact protection, yet be unobtrusive and comfortable so users wear it, and when they do, it enables them to easily talk, breathe and drink.

SUMMARY OF THE INVENTION

A mouth guard has a bite line separating an outer portion and an inner portion. The bite line extends through a line of symmetry of the guard. The line of symmetry divides the guard into a first half and a second half. The guard has a plurality of sets of open spaces in the outer portion. At least some of the sets of open spaces are comprised of three arrays of open spaces arranged in a triangular pattern, where each array has three open spaces.

BRIEF DESCRIPTION OF THE DRAWINGS

The features of the subject invention will be better understood in the context of the detailed description, in conjunction with the drawings.

DETAILED DESCRIPTION OF THE PREFERRED EMBODIMENTS

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions, directions or other physical characteristics relating to the embodiments disclosed are not to be considered as limiting, unless the claims expressly state otherwise.

Figure 1:
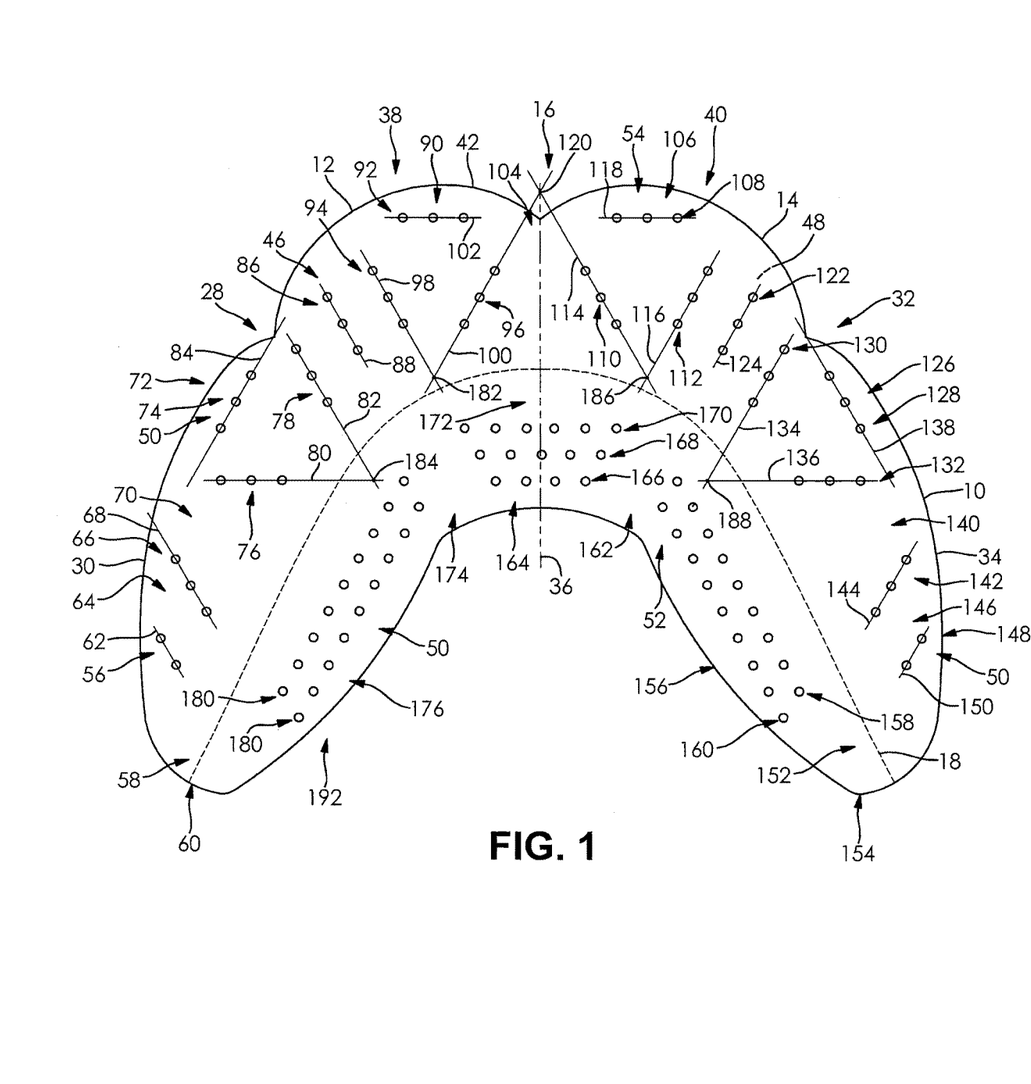
FIG. 1 depicts one embodiment of a plan view of an impact energy absorbing mouth guard in a first state.

Turning now to FIG. 1, one embodiment of a dental appliance 10, also referred to a mouth guard herein, is depicted. A preferred embodiment of the dental appliance 10 is shown in a flattened, first state. The appliance 10 is a one-piece, unitary and integrally formed sheet of material. In one embodiment, the appliance 10 may be 0.25 mm to 2 mm thick and fabricated from a thermoplastic polymer matrix material. Such a material is widely available, inexpensive and readily disposable when the appliance 10 is exhausted.

The appliance 10 may be produced by injection molding, but other production methods are permissible. In one embodiment, the appliance 10 may be produced by 3-D printing. Alternatively, a portion of the appliance 10 may be injected molded and another portion produced by 3-D printing.

The appliance 10 comprises a first front flap 12 and a second front flap 14, which together are called a maxillary flap. A forward cusp 16 is located between the two flaps 12, 14. The cusp 16 extends inwardly into the appliance 10 at least partially dividing the first front flap 12 and the second front flap 14. The cusp 16 extends inwardly toward, but preferably does not reach, a bite line 18.

Figure 3:
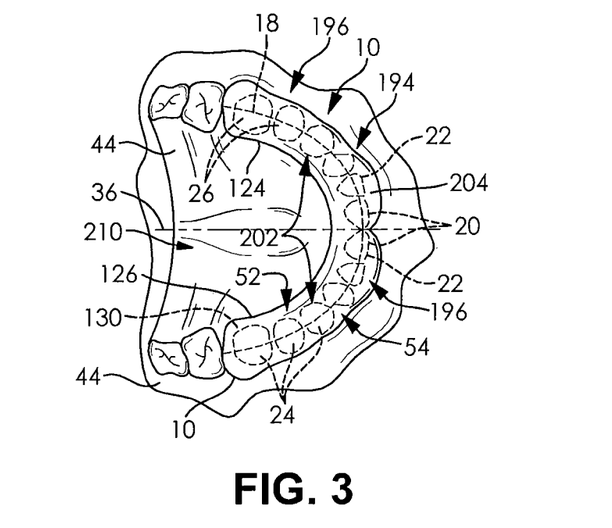
FIG. 3 depicts the mouth guard of FIG. 1 is a second state on the dentition of a user.

The bite line 18 is the line on the appliance 10 along which the incisal edges 20 of the incisors 22 and the tips of the occluding surfaces 24 of the posterior teeth 26 come in contact with the appliance 10, as shown in FIG. 3. Together, these edges 20 and surfaces 24 are called crowns herein. The bite line 18 is generally arch-shaped to be complementary to the arrangement of teeth in a wearer's mouth.

A first side cusp 28 further defines the first front flap 12. The first side cusp 28 is located between the first front flap 12 and a first outer side flap 30. The first side cusp 28 extends inwardly into the appliance 10 toward the bite line 18. The first side cusp 28 may extend inwardly into the appliance 10 at the same depth as the forward cusp 16 or to a greater or lesser extent.

A second side cusp 32 further defines the second front flap 14. The second side cusp 32 is located between the second front flap 14 and a second outer side flap 34. The second side cusp 32 extends inwardly into the appliance 10 toward the bite line 18. The second side cusp 32 may extend inwardly into the appliance 10 at the same depth as the forward cusp 16 or to a greater or lesser extent.

In the embodiment depicted in FIG. 1, a line of symmetry 36 extends from the forward cusp 16 to equally divide the appliance 10 into a first half 38 and a second half 40, which are symmetric with one another. More particularly, the line of symmetry 36 results in a mirror image between the first half 38 and the second half 40. It is permissible, however, for the first half 38 to be non-symmetrical with the second half 40.

Figure 4:
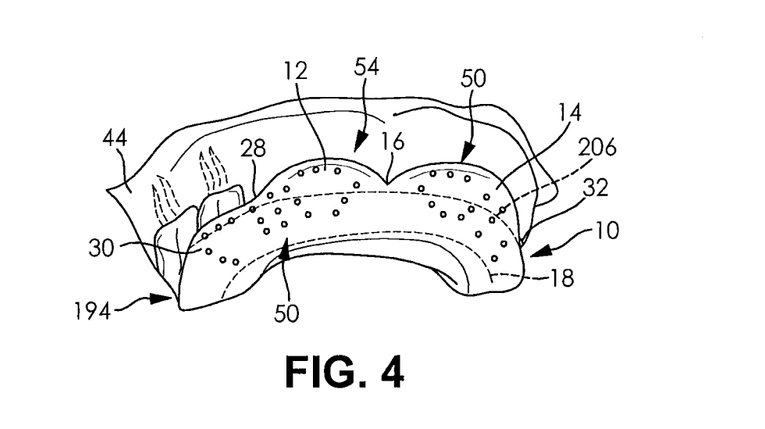
FIG. 4 provides a second view of the mouth guard of FIG. 3 in the second state on the dentition of a user.

A perimeter 42 defines the first front flap 12, the second front flap 14, and the side flaps 30, 34. The perimeter 42 is preferably rounded, or curvilinear. This embodiment is envisioned to impose the least, if any, discomfort to the wearer of the dental appliance 10 since it has no sharp corners or edges to embed into the soft gum tissue 44, as shown in FIGS. 3 and 4.

The appliance 10 has a first planar side 46 and a second planar side 48 in the first state. The second planar side 48 is opposite the first planar side 46. The second planar side 48 may be parallel to the first planar side 46. Therefore, in the depicted embodiment, the appliance 10 has a substantially constant thickness. The appliance 10 may, however, not have a substantially constant thickness.

For example, the entire thickness of the appliance 10 may be increased, or it may be increased in certain areas. 3-D printing may be used to increase the thickness of the appliance 10 to 1.6-3 mm by depositing a thermoplastic polymer matrix on top of an existing layer.

Figure 2A:
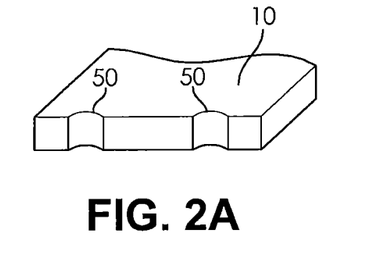
FIG. 2A depicts a partial schematic perspective view of a portion of the guard of FIG. 1 in a first condition.
Figure 2B:
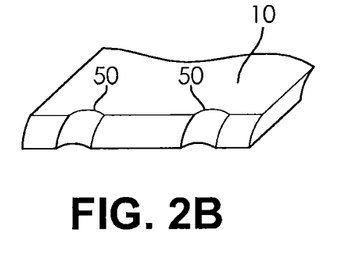
FIG. 2B depicts a partial schematic perspective view of the portion of the guard of FIG. 1 in a second condition.

The appliance 10 depicted in FIG. 1 has a plurality of open spaces 50 on an inner portion 52 and an outer portion 54 of the bite line 18. The open spaces 50 extend through the appliance 10 from the first side 46 to the second side 48, as shown in FIGS. 1, 2A and 2B.

The open spaces 50 are depicted as cylindrical with circular cross-sections, however, it can be appreciated that other shapes, numbers, designs and/or orientations are permissible. It is preferred that regardless of the open spaces 50 selected, that the design selected is symmetrical about the line symmetry 36, but it is not required.

The open spaces 50 are shown to have circular openings at the sides 46, 48, however, other shapes of the open spaces 50 are permissible. Further, while FIG. 1 depicts the open spaces 50 having all the same size and shape, it can be appreciated that the size and shape of the open spaces 50 can vary. As shown in FIG. 2A, the open spaces 50 extend through the appliance 10 with a cylindrical cross section. The opens spaces 50 in FIG. 1 are in the condition where a force has not been applied to the appliance 10.

The open spaces 50 are located in a preferred pattern as shown in FIG. 1. Beginning with the area of the outer portion 54 of the first outer side flap 30, there is a first set of open spaces 56. Preferably, there is a first unperforated area 58 between the perimeter 42 of the appliance 10 and the first set of open spaces 56. The first unperforated area 58 extends between the first set of open spaces 56 and a rearmost portion 60 of the first half 38 of the appliance 10. The first unperforated area 58 extends from the outer portion 54 across the bite line 18 to the inner portion 52 of the appliance 10.

The first set of open spaces 56 comprise two open spaces. The two open spaces are aligned with one another. An imaginary line 62 extending through the centers of the two open spaces extends outward though the outer portion 54 and the perimeter 42. The first set of open spaces 56 are located outboard of the bite line 18 in the outer portion 54 of the appliance 10 and on the first half 38 of the appliance 10.

Moving forward from the rearmost portion 60 of the first half 38 the appliance 10 along the perimeter 42 beyond the first set of open spaces 56, a second unperforated area 64 is provided. The second unperforated area 64 extends between the first set of open spaces 56 and a second set of open spaces 66.

The second set of open spaces 66 comprises three open spaces. The three open spaces are aligned with one another. An imaginary line 68 extending through the centers of the three open spaces extends outward through the outer portion 54 and the perimeter 42. The imaginary line 68 extending through the three open spaces is a parallel the imaginary line 62 extending through the first set of open spaces 56. The second set of open spaces 66 are located outboard of the bite line 18 in the outer portion 54 of the appliance 10 and on the first half 38 of the appliance 10.

Moving forward from the second set of open spaces 66 along the perimeter 42 beyond the first set of open spaces 56, a third unperforated area 70 is provided. The third unperforated area 70 extends between the second set of open spaces 66 and a third set of open spaces 72. The third unperforated area is located outboard of the bite line 18 in the outer portion 54 of the appliance 10 and on the first half 38 of the appliance 10.

The third set of open spaces 72 is comprised of three arrays of open spaces arranged in a triangular pattern. A first array 74 comprises a base of the triangle. The first array 74 is located adjacent the perimeter 42 and generally parallel the perimeter 42. A second array 76 and a third array 78 comprises the sides of the triangle. The second and third arrays 76, 78 are positioned at acute angles with respect to the first array 74. The acute angle may be such as approximately 60 degrees.

Imaginary lines 80, 82 extending through the centers of the open spaces of the second and third arrays 76, 78 diverge from one another as they extend outwardly through the outer portion 54 and the perimeter 42. The imaginary lines 80, 82 extending through the second and third arrays 76, 78 are not parallel the imaginary lines 62, 68 extending through the first and second set of open spaces 56, 66.

The open spaces of the second and third arrays 76, 78 nearest the first array 74 are almost aligned with one another. In other words, an imaginary line 84 extends through the open spaces of the first array 74, the imaginary line 84 would almost go through the open spaces of the second and third arrays 76, 78.

The third set of open spaces 72 are located outboard of the bite line 18 in the outer portion 54 of the appliance 10 and on the first half 38 of the appliance 10. Each of the arrays 74, 76, 78 of the third set of open spaces 72 is comprised of three individual open spaces.

Moving forward from the third set of open spaces 72 along the perimeter 42, a fourth set of open spaces 86 is provided. The fourth set of open spaces 86 comprises three open spaces. The three open spaces are aligned with one another. An imaginary line 88 extending through the centers of the three open spaces extends outward through the outer portion 54 and the perimeter 42. The imaginary line 88 extending through the three open spaces is a parallel the imaginary lines 62, 68 extending through the first set of open spaces 56 and the second set of open spaces 66. The fourth set of open spaces 86 are located outboard of the bite line 18 in the outer portion 54 of the appliance 10 and on the first half 38 of the appliance 10.

The third array 78 of the third set of open spaces 72 is oriented parallel to the fourth set of open spaces 86. Further, at least some of individual open spaces of the third array 78 of the third set of open spaces 72 are aligned with the individual open spaces of the third set of open spaces 72.

Moving forward from the fourth set of open spaces 86 along the perimeter 42, a fifth set of open spaces 90 is provided. The fifth set of open spaces 90 is comprised of three arrays of open spaces arranged in a triangular pattern. A first array 92 comprises a base of the triangle. The first array 92 is located adjacent the perimeter 42 and generally parallel the perimeter 42. A second array 94 and third array 96 comprises the sides of the triangle. The second and third arrays 94, 96 are positioned at acute angles with respect to the first array 92.

Imaginary lines 98, 100 extending through the centers of the open spaces of the second and third arrays 94, 96 diverge from one another as they extend outwardly through the outer portion 54 and the perimeter 42.

The open spaces of the second and third arrays 94, 96 nearest the first array 92 are not aligned with one another. In other words, if an imaginary line 102 extends through the open spaces of the first array 92, the imaginary line 102 would not go through the open spaces of the second and third arrays 94, 96; there is an offset between the open spaces of the second and third arrays 94, 96 and the first array 92.

The fifth set of open spaces 90 are located outboard of the bite line 18 in the outer portion 54 of the appliance 10 and on the first half 38 of the appliance 10. More particularly, the fifth set of open spaces 90 is located in the first front flap 12. Each of the arrays 92, 94, 96 of the fifth set of open spaces 90 is comprised of three individual open spaces.

The second array 94 of the fifth set of open spaces 90 is oriented parallel to the fourth set of open spaces 86. Further, the individual open spaces of the second array 94 of the fifth set of open spaces 90 are aligned with the individual open spaces of the fourth set of open spaces 86.

Moving from the fifth set of open spaces 90 along the perimeter 42, a fourth unperforated area 104 is provided. The fourth unperforated area 104 extends between the fifth set of open spaces 90 and a sixth set of open spaces 106. The fourth unperforated area 104 is located radially inward from the forward cusp 16 and between the forward cusp 16 and the bite line 18.

The sixth set of open spaces 106 is comprised of three arrays of open spaces arranged in a triangular pattern. A first array 108 comprises a base of the triangle. The first array 108 is located adjacent the perimeter 42 and generally parallel the perimeter 42. A second array 110 and third array 112 comprises the sides of the triangle. The second and third arrays 110, 112 are positioned at acute angles with respect to the first array 108.

Imaginary lines 114, 116 extending through the centers of the open spaces of the second and third arrays 110, 112 diverge from one another as they extend outwardly through the outer portion 54 and the perimeter 42.

The open spaces of the second and third arrays 110, 112 nearest the first array 108 are not aligned with one another. In other words, if an imaginary line 118 extends through the open spaces of the first array 108, the imaginary line 118 would not go through the open spaces of the second and third array 110, 112; there is an offset between the open spaces of the second and third arrays 110, 112 and the first array 108.

The sixth set of open spaces 106 are located outboard of the bite line 18 in the outer portion 54 of the appliance 10 and on the second half 40 of the appliance 10. More particularly, the sixth set of open spaces 106 is located in the second front flap 14. Each of the arrays 108, 110, 112 of the sixth set of open spaces 106 is comprised of three individual open spaces.

Imaginary lines 100, 114 extending from the second array 110 of the sixth set of open spaces 106 and the third array 96 of the fifth set of open spaces 90 intersect at a point 120 outside of the perimeter 42 of the appliance 10. The intersection point 120 is located directly outward from the forward cusp 16.

Moving rearward from the sixth set of open spaces 106 along the perimeter 42, a seventh set of open spaces 122 is provided. The seventh set of open spaces 122 comprises three open spaces. The three open spaces are aligned with one another. An imaginary line 124 extending through the centers of the three open spaces extends outward through the outer portion 54 and the perimeter 42. The imaginary line 124 extending through the three open spaces is a parallel the imaginary line 116 extending through the third array 112 of the sixth set of open spaces 106. The seventh set of open spaces 122 are located outboard of the bite line 18 in the outer portion 54 of the appliance 10 and on the second half 40 of the appliance 10. Further, the individual open spaces of the third array 112 of the sixth set of open spaces 106 are aligned with the individual open spaces of the seventh set of open spaces 122. The third array 112 of the sixth set of open spaces 106 is oriented parallel to the seventh set of open spaces 122.

Moving downwardly, or rearwardly, along the perimeter 42, an eighth set of open spaces 126 is provided. The eighth set of open spaces 126 is comprised of three arrays of open spaces arranged in a triangular pattern. A first array 128 comprises a base of the triangle. The first array 128 is located adjacent the perimeter 42 and generally parallel the perimeter 42. A second and third array 130, 132 comprises the sides of the triangle. The second and third arrays 130, 132 are positioned at acute angles with respect to the first array 128. The acute angle may be such as approximately 60 degrees.

Imaginary lines 134, 136 extending through the centers of the open spaces of the second and third arrays 130, 132 diverge from one another as they extend outwardly through the outer portion 54 and the perimeter 42.

The open spaces of the second and third arrays 130, 132 nearest the first array 128 are almost aligned with one another. In other words, if an imaginary line 138 extends through the open spaces of the first array 128, the imaginary line 138 would almost go through the open spaces of the second and third arrays 130, 132.

The eighth set of open spaces 126 are located outboard of the bite line 18 in the outer portion 54 of the appliance 10 and on the second half 40 of the appliance 10. Each of the arrays 128, 130, 132 of the eighth set of open spaces 128 is comprised of three individual open spaces.

The second array 130 of the eighth set of open spaces 126 is oriented parallel to the seventh set of open spaces 122. Further, the individual open spaces of the second array 130 of the eighth set of open spaces 126 are aligned with the individual open spaces of the seventh set of open spaces 122.

Moving downwardly from the eighth set of open spaces 126 along the perimeter 42, a fifth unperforated area 140 is provided. The fifth unperforated area 140 extends between the eighth set of open spaces 126 and a ninth set of open spaces 142. The fifth unperforated area 140 is located radially inward from the perimeter 42 and the bite line 18.

The ninth set of open spaces 142 comprises three open spaces. The three open spaces are aligned with one another. An imaginary line 144 extending through the centers of the three open spaces extends outward through the outer portion 54 and the perimeter 42. The ninth set of open spaces 142 are located outboard of the bite line 18 in the outer portion 54 of the appliance 10 and on the second half 40 of the appliance 10.

Moving downward from the ninth set of open spaces 142 along the perimeter 42, a sixth unperforated area 146 is provided. The sixth unperforated area 146 extends between the ninth set of open spaces 142 and a tenth set of open spaces 148.

The tenth set of open spaces 148 comprise two open spaces. The two open spaces are aligned with one another. An imaginary line 150 extending through the centers of the two open spaces extends outward though the outer portion 54 and the perimeter 42. The tenth set of open spaces 148 are located outboard of the bite line 18 in the outer portion 54 of the appliance 10 and on the second half 40 of the appliance 10.

The imaginary line 150 extending through the tenth set of open spaces 148 is parallel the imaginary line 144 extending through the ninth set of open spaces 142. These two imaginary lines 150, 144 are not parallel with the imaginary line 134 extending from the third array 132 in the eighth set of open spaces 126.

Moving rearward from the tenth set of open spaces 148 along the perimeter 42, a seventh unperforated area 152 is provided. The seventh unperforated area 152 extends between the tenth set of open spaces 148 to a rearmost portion 154 of the second half 40 of the appliance 10. The tenth set of open spaces 148 extends from the outer portion 54 across the bite line 18 to the inner portion 52 of the appliance 10.

Inboard, or rearward, of the bite line 18, three sets of open spaces are provided in the inner portion 52 of the appliance 10. Continuing with the numbering from the sets of open spaces from the outer portion 54 of the appliance 10, the inner portion 52 has an eleventh set of open spaces 156.

The eleventh set of open spaces 156 is preferably comprised of an inner row 158 and an outer row 160 of individual open spaces. The inner row 158 is closest to the bite line 18 while the outer row 160 is closest to the perimeter 42. The inner and outer rows 158, 160 are parallel one another and the bite line 18, but the inner row 158 is advanced forward of the outer row 160. In the depicted embodiment, the inner row 158 is advanced at least one individual open space beyond the outer row 160 in the forward direction. The forward advancement of the inner row 158 compared with the outer row 160 results in the individual open spaces of the inner row 158 being misaligned with the individual open spaces of the outer row 160. In other words, the individual open spaces of the inner row 158 are located between the individual spaces of the outer row 160, but there is a gap between the rows 158, 160. Preferably, the inner and outer rows 158, 160 have the same number of individual open spaces. As shown in the FIG. 1, each row 158, 160 has nine open spaces.

In the depicted embodiment, the inner and outer rows 158, 160 are located inboard of, and generally aligned with, the eighth, ninth and tenth sets of open spaces 126, 142, 148 and the fifth and sixth unperforated areas 140, 146.

Moving forward along the perimeter 42 from the eleventh set of open spaces 156, an eighth unperforated area 162 is provided. The eighth unperforated area 162 is located between the perimeter 42 and the bite line 18 in the inner portion 52 of the appliance 10. Further, the eighth unperforated area 162 is located between the eleventh set of open spaces 156 and a twelfth set of open spaces 164.

The twelfth set of open spaces 164 is comprised of three rows of open spaces. The rows are positioned transverse the line of symmetry 36 of the appliance 10. Further, the rows are bisected by the line of symmetry 36 of the appliance 10.

The first row 166 is the rearmost, or outward most, and is located adjacent the perimeter 42. The first row 166 is located parallel the perimeter 42. The first row 166 is comprised of four individual open spaces, with two open spaces on one side of the line of symmetry 36 and the other two open spaces on the other side of the line of symmetry 36.

The second row 168 is located inboard of the first row 166. Preferably, the individual open spaces of the second row 168 are offset from the individual open spaces of the first row 166. In other words, the individual open spaces of the second row 168 are located between the individual spaces of the first row 166, but there is a gap separating the rows 166, 168. The second row 168 is comprised of five individual open spaces with two open spaces on one side of the line of symmetry 36, two open spaces on the other side of the line of symmetry 36 and one open space bisected by the line of symmetry 36.

The third row 170 is located inboard of the second row 168. Preferably, the individual open spaces of the third row 170 are offset from the individual open spaces of the second row 168. In other words, the individual open spaces of the third row 170 are located between the individual spaces of the second row 168, but there is a gap separating the rows 168, 170. The third row 170 is comprised of six individual open spaces with three open spaces on one side of the line of symmetry 36, and three open spaces on the other side of the line of symmetry 36. The third row of open spaces 170 is located outboard of the bite line 18 with an unperforated gap 172 separating the third row 170 from the bite line 18. The third row of open spaces 170 is located inboard from the two rows 158, 160 from the eleventh set of open spaces 156. The third row of open spaces 170 is located closer to the bite line 18 than the inner row 158 of the eleventh set 156. The first row 166 of the twelfth set 164 and the outer row 160 of the eleventh set 156 are located approximately the same distance from the perimeter 42.

The twelfth set of open spaces 164 is located across the bite line 18 from the fourth unperforated area 104 and the fifth and sixth sets of open spaces 90, 106. Overall, the rows of the twelfth set of open spaces 164 forms a generally triangular shape.

Moving rearwardly, or backward, along the perimeter 42 from the twelfth set of open spaces 164, a ninth unperforated area 174 is provided. The ninth unperforated area 174 is located between the perimeter 42 and the bite line 18 in the inner portion 52 of the appliance 10. Further, the ninth unperforated area 174 is located between the twelfth set of open spaces 164 and a thirteenth set of open spaces 176.

The thirteenth set of open spaces 176 is preferably comprised of an inner row 178 and an outer row 180 of individual open spaces. The inner row 178 is closest to the bite line 18 while the outer row 180 is closest to the perimeter 42. The inner and outer rows 178, 180 are parallel one another and the bite line 18, but the inner row 178 is advanced forward of the outer row 180. In the depicted embodiment, the inner row 178 is advanced at least one individual open space beyond the outer row 180 in the forward direction. The forward advancement of the inner row 178 compared with the outer row 180 results in the individual open spaces of the inner row 178 being misaligned with the individual open spaces of the outer row 180. In other words, the individual open spaces of the inner row 178 are located between the individual spaces of the outer row 180, but there is a gap between the rows 178, 180. Preferably, the inner and outer rows 178, 180 have the same number of individual open spaces. As shown in the FIG. 1, each row 178, 180 has nine open spaces.

In the depicted embodiment, the inner and outer rows 178, 180 are located inboard of, and generally aligned with the first, second and third sets of open spaces 56, 66,72 and the second and third unperforated areas 64, 70.

As made clear by the above description, the appliance 10 is symmetrical about the line of symmetry 36. Thus, the first, second, third, fourth and fifth, and thirteenth sets of open spaces 56, 66, 72, 86, 90, 176 are symmetrical with the tenth, ninth, eighth, seventh and sixth set of open spaces, 146, 142, 126, 122, 106 respectively. The twelfth set of open spaces 164 is symmetrical about itself along the line of symmetry 36. Further, the first, second, third, and ninth unperforated areas 58, 64, 70, 174, and the rearmost portion of the first half 60 of the appliance 10 are symmetrical with the seventh, sixth, fifth and eighth unperforated areas 152, 146, 140, 162, and the rearmost portion of the second half 154 of the appliance 10, respectively. The fourth unperforated area 104 is symmetrical about itself along the line of symmetry 36.

The bite line 18 is free of open spaces.

The imaginary lines 98, 100 extending through the centers of the open spaces of the second and the third arrays 94, 96 in the fifth set of open spaces 90 intersect at a first point 182 in the first half 38 of the appliance 10. The imaginary lines 80, 82 extending through the centers of the open spaces of the second and the third arrays 76, 78 in the third set of open spaces 72 intersect at a second point 184 in the first half 38 of the appliance 10. The first and the second points 182, 184 are not the same.

The imaginary lines 114, 116 extending through the centers of the open spaces of the second and third arrays 110, 112 in the sixth set of open spaces 106 intersect at a third point 186 in the second half 40 of the appliance 10. The imaginary lines 136, 134 extending through the centers of the open spaces of the second and the third arrays 130, 132 in the eighth set of open spaces 128 intersect at a fourth point 188 in the second half 40 of the appliance 10. The third and fourth points 186, 188 are not the same.

Fourth point 188 and second points 184 are located on the inner portion 52. Third point 186 and first point 182 are located on the outer portion 54.

As mentioned, the fourth set of open spaces 86 is located between the third set of open spaces 72 and the fifth set of open spaces 90. The fourth set of open spaces 86 is parallel the second array 94 in the fifth set of open spaces 90 and the third array 78 in the third set of open spaces 72.

The first and second sets of open spaces 56, 66 in the first half 38 are parallel the fourth set of open spaces 86.

As mentioned above, the seventh set of open spaces 122 is located between the sixth set of open spaces 106 and the eighth set of open spaces 126. The seventh set of open spaces 122 is parallel the third array 112 in the sixth set of open spaces 106 and the second array 130 in the eighth set of open spaces 126.

The seventh set of open spaces 122 is parallel the ninth and tenth sets of open spaces 142, 148, all in the second half 40 of the appliance 10.

While clear from at least FIG. 1, the fifth set of open spaces 90 and the sixth set of open spaces 106 are mirror images of one another. And, the third set of open spaces 72 and eighth set of open spaces 126 are mirror images of one another.

The appliance 10 depicted in FIG. 1 and described above has been found to have superior force absorbing design. It has been found that a three open space pattern, where the three open spaces are aligned in a straight line with one another has been found to be particularly effective in absorbing force. The three open space pattern is found in the arrays of the third, fifth, sixth, and eighth set of open spaces 72, 90, 106, 126, as well as the second, fourth, seventh and ninth set of open spaces 66, 86, 122, 142. The force absorbing feature has been also found to be particularly effective when three, three open space pattern of an array are oriented in a triangular shape, as described in the third, fifth, sixth and eighth sets of open spaces 72, 90, 106, 126. As noted above, the twelfth set of open spaces is also in a generally triangular shape for force absorption 164.

It is thus an intentional part of the design for the fifth and sixth sets of open spaces 90, 106 to be arranged in the first front flap 12 and the second front flap 14, where a force impact is likely to be experienced.

It is also an intentional part of the design that while the third and eighth set of open spaces 72, 126 match in terms of layout and spacing, and the fifth and sixth set of open spaces 90, 106 match in terms of layout and spacing, that between these sets they have a different layout and spacing. The differences in layout and spacing of these sets of open spaces are described above. It has been found by applying these differences that force absorption and dissipation is increased compared with prior art designs.

While all of the sets of open spaces are beneficial for fitting the guard, saliva flow and unhindered breathing and talking, it has been found that the eleventh, twelfth and thirteenth 156, 164, 176 set of open spaces are particularly advantageous in this regard.

A method of using the dental appliance 10 described above to protect the dentition of a wearer follows.

The appliance 10 is initially in a first planar state 192, as shown in FIG. 1. At room temperature, the appliance 10 is rigid. The appliance 10 may be heated such as by convection, conduction and/or radiation until it is pliable. Once pliable, the appliance 10 is located adjacent the dentition of a patient. In the preferred embodiment, the appliance 10 is located adjacent the maxilla (upper dentation) into a second, non-planar state 194 described below, and depicted in FIGS. 4 and 5. Alternatively, the appliance 10 may be located adjacent the mandible (lower jaw), or a first sheet can be located adjacent the maxilla and a second sheet can be located adjacent the mandible.

Continuing with the embodiment wherein the appliance 10 is located just adjacent the maxilla, the crowns of the dentition 20, 24 are positioned adjacent the bite line 18 on the appliance 10. The appliance 10 is moved into contact with the dentition 20, 24 and then molded around the dentition 20, 24. More particularly, the first and second front flaps 12, 14 are molded in front of the outward facing surfaces 196 of the dentition. Similarly, the outer side flaps 30, 34 are molded in front of the outward facing surface 196 of the dentition. Preferably, the first and second front flaps 12, 14, and also the outer side flaps 30, 34, are located vertically, or with a small angle variance from vertical (e.g. 10 degrees), from the bite line 18. In other words, the flaps 12, 14, 30, 34 are located parallel, or approximately parallel, the outward facing surfaces 196. The flaps 12, 14, 30, 34 are preferably located in this orientation because it encases the dentitions to protect them and it keeps the appliance 10 close to the dentitions so that it is easier for the wearer to speak, drink and breath with the appliance 10 in place. In other words, the appliance 10 does not interfere with the lips, tongue or palate of the user.

The appliance 10 also comprises a first inner side flap 198 and a second inner side flap 200. The flaps 198, 200 are bounded by the perimeter 42 and the bite line 18. As shown in FIG. 1, the flaps 198, 200 are symmetrical across the line of symmetry 36, but non-symmetrical flaps are permissible.

The first inner side flap 198 and the second inner side flap 200 are molded upwardly so they are positioned behind rearward facing surfaces 200 of the dentition. The flaps 198, 200 are located vertically, or within a small angle variance from vertical (e.g. 10 degrees) from the bite line 18. In other words, the flaps 198, 200 are located parallel, or approximately parallel, the rearward facing surfaces 202.

Figure 5:
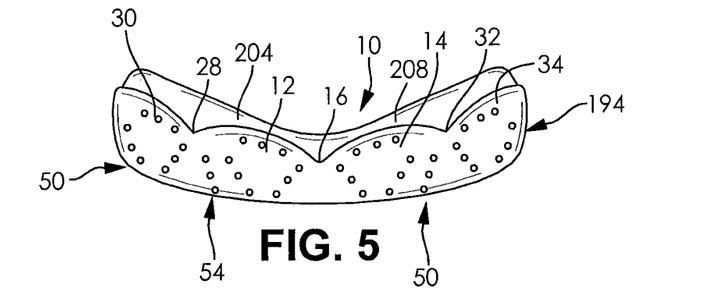
FIG. 5 depicts the mouth guard in the second state but not located on the dentition of a user.

The upward location of the flaps 12, 14, 30, 34, 198, 200 effectively encases the outward and rearward surfaces 196, 202 of the maxilla dentition in a channel 204, which can be appreciated from FIGS. 3 and 5. The channel 204 is curved along the bite line 18 so as to be complimentary to the wearer's dentition. The channel 204 protects the outward and rearward facing surfaces 196, 202 as well as the incisal edges 20 and occluding surfaces 24 of many of the wearer's dentition.

When the appliance 10 is fit onto the dentition of a wearer, the forward cusp 16 falls centrally between the two maxillary central incisor teeth 22. When formed to the dentitions, the first and second front flaps 12, 14 cross over a maxillary teeth-gum intersection line 206 and extend over the soft gum tissue 44, as shown in FIG. 4. It has been found that when the appliance 10 extends over the maxillary teeth-gum intersection line 206, the appliance 10 more robustly can protect the dentition from being moved during force application. In one embodiment, the flaps 12, 14 extend beyond the teeth-gum intersection line 206 approximately 0.25 to 0.35 mm. While one range of extension is mentioned above, it can be appreciated that this dimension can be larger or smaller to cover more or less of the soft gum tissue 44.

The flaps 12, 14, 30, 34, 198, 200 can be manually manipulated to position them as described above. In addition, the wearer can draw air through the open spaces 50. The vacuum created by the wearer by drawing the air through the spaces 50 pulls the pliable appliance 10 into conformal contact with the dentition.

The manual manipulation and/or the vacuum applied to the appliance 10 causes an interior surface 208 of the appliance 10 to mold into intimate contact with the outward facing surfaces 198 and/or rearward facing surfaces 202 of the dentition. As the appliance 10 cools, it may shrink into further contact with the dentition. During cooling, the appliance 10 hardens into a shape that well adheres to the contours of every unique tooth. This adherence ensures the appliance 10 does not become dislodged. In addition, the adherence and thin dimension of the appliance 10 provides a clear, unobstructed view of the wearer's mouth, voice box and trachea.

The open spaces 50 in the appliance 10 provide a conformal fit of the appliance 10 onto any dentition and enable a secure custom fit by changing in size and in shape in all or some when the appliance 10 is in the pliable condition. The secure, custom fits enables the appliance to remain fixed on the dentition. The open spaces 50 allow the softened thermopolymer material to be formed into a three-dimensional shape without buckling, bunching, creasing, or bulging.

Based on the above-provided description and FIG. 3, it can be appreciated that there is no portion of the appliance 10 that spans the upper palate 210 of the user. Instead, the appliance 10 terminates at the flaps 12, 14, 30, 34, 198, 200 before it extends across the upper palate 210. Thus, there is a gap between the flaps 12, 14, 30, 34, 198, 200 that leaves the upper plate 210 exposed.

If the appliance 10 has to be re-fitted after it has cooled and hardened, it can be warmed to its softening point and the fitting process can be repeated because its second state is only a semi-permanent state.

FIG. 2B depicts two of the open spaces 50 of FIG. 1 but subject to a force. The force deforms the open spaces 50 resulting in dissipation of the force. In FIG. 2B, the open space 50 is deformed as a result of one kind of force from a circular cross-section to an oval cross-section. The shape change of the open spaces 50 expends some or all of the energy of the force traveling through the appliance 10.

In one example, because the appliance 10 maintains a constant volume, when a force encounters an open space 50, the deformed open space 50 compresses the adjacent open spaces 50. The combination of deformation and compression of the open spaces 50 results in force dissipation.

One kind of force, such as caused by a shearing action, may travel through the appliance 10 in a wave or waves. The waves may travel along an outer surface of the appliance 10 and/or through the appliance 10.

Another kind of force is a force that is normal to the appliance 10. The normal force can be applied substantially at once, it can be repeated, and/or it can increase or decrease in intensity.

While FIG. 2B depicts the two open spaces 50 both deformed to dissipate a force, it can be appreciated that only one or the other might be deformed. Further, while FIG. 2B depicts the open spaces 50 deformed into oval cross-sections, they may be deformed into other shapes and/or the shapes do not have to match one another.

The open spaces 50 are located in the appliance 10 to maximize tensile strength of the appliance 10 without exposing any of the protected dental surfaces to the unprotected teeth on the opposite jaw. The locations of the open spaces 50 also optimize saliva flow around the dentitions, which improves comfort. More particularly, saliva can be sucked through the open spaces 50. The open spaces 50 also function to improve breathing by allowing the appliance 10 to be thinner and thus take up less space in the mouth.

Based on the foregoing, it can be appreciated that the appliance material, the location of that material on the wearer's dentition as described herein, the open spaces, and/or plastic and/or elastic deformation effectively diminishes forces transmitted in the axial (normal) direction, as well as in the horizontal direction, with respect to the dental surfaces.

Figures 6, 7, 8, 9, 10:
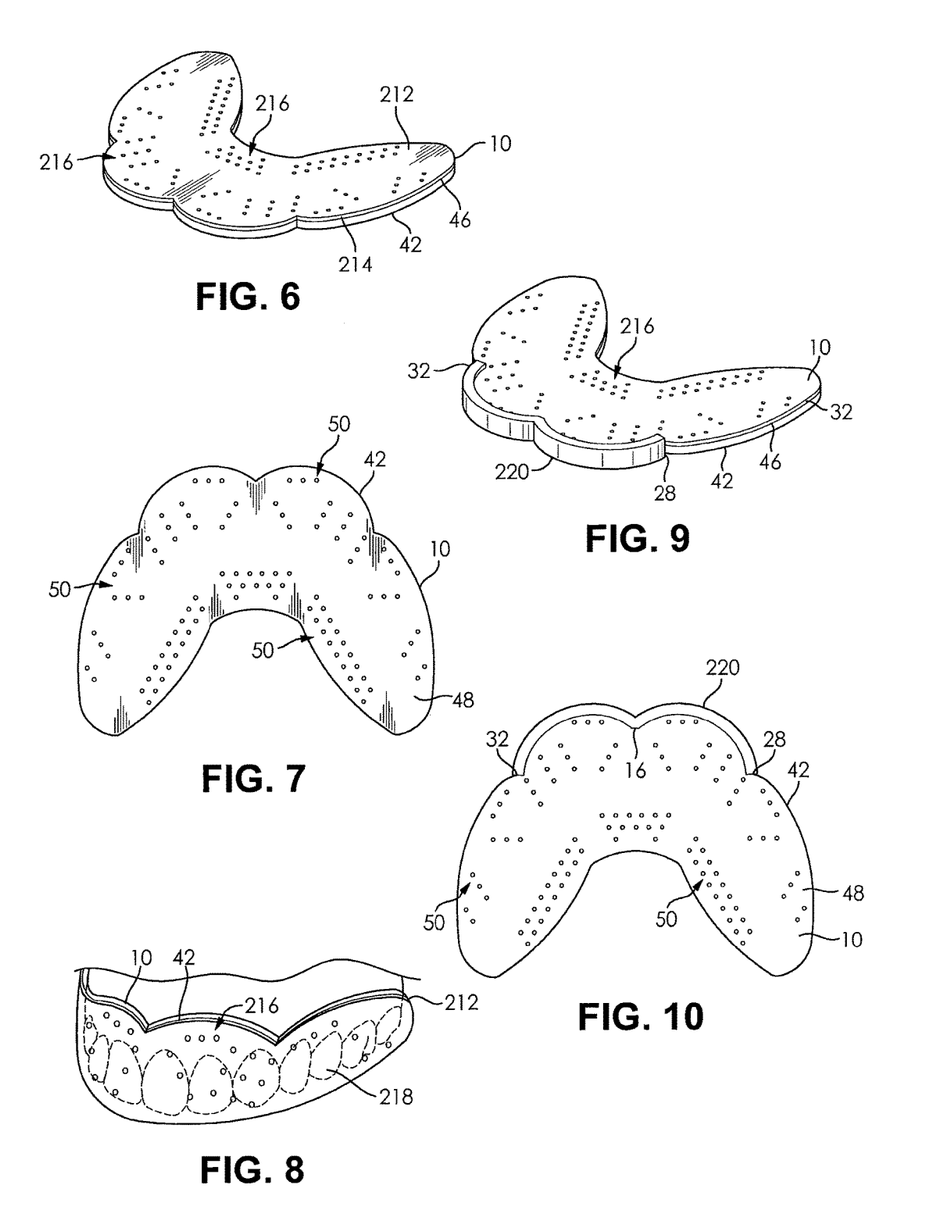
FIG. 6 depicts a perspective view of another embodiment of the mouth guard.
FIG. 7 depicts a bottom view of the mouth guard of FIG. 6.
FIG. 8 depicts a perspective view of the mouth guard of FIG. 6 on the dentition of a user.
FIG. 9 depicts a perspective view of another embodiment of the mouth guard.
FIG. 10 depicts a bottom view of the mouth guard of FIG. 9.

Turning now to FIGS. 6, 7 and 8 another embodiment of the appliance 10 is depicted. In these figures, the appliance 10 is the same as described above and depicted in the figures, except as noted below. Thus, like reference numbers will be used for the same features.

A polymer layer 212 is added to the first planar side 46 of the appliance 10. The polymer layer 212 extends continuously across the first planar side 46. The polymer layer 212 is not located on the second planar side 48. The polymer layer 212 stops at the perimeter 42 and thus an edge 214 of the polymer layer 212 is coplanar with the perimeter 42 of the appliance 10. The polymer layer 212 has a shape complementary to the shape of the appliance 10.

Preferably, the same pattern of the plurality of open spaces 50 in the appliance 10 is provided in the polymer layer 212. In other words, the polymer layer 212 may have openings 216 corresponding to all of the sets of open spaces 56, 66, 72, 86, 90, 106, 122, 126, 142, 148, 156, 164, 176 in the appliance 10.

The polymer layer 212 may be a different material than the material for the appliance 10. One such material may be ethylene vinylacetate (EVA) but other thermoplastic polymers of a low molecular weight may be used.

The polymer layer 212 has a uniform thickness across the appliance 10. The polymer layer thickness may be less than the thickness of the appliance 10.

As can be appreciated from FIG. 8, the polymer layer 212 is designed to be opposite the dentitions 218 of the user. In other words, the polymer layer 212 is designed to be located directly against the inner lip of the user. The second planar side is located in direct contact with the dentitions 218 of the user.

The polymer layer 212 functions as a protective layer for the soft tissues of the user. More particularly, the polymer layer 212 is designed to be located between the soft tissues of the user, such as gums and lips, and the appliance 10. The polymer layer 212 protects the soft tissues of the user from the relatively hard appliance 10 with some cushioning effect. In addition, the polymer layer 212 provides a softer edge which is less likely to irritate, rub into and/or damage the soft tissues of a user.

Figure 11:
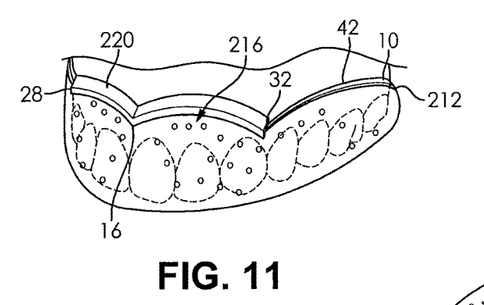
FIG. 11 depicts a perspective view of the mouth guard of FIG. 9 on the dentition of a user.

Turning now to FIGS. 9, 10 and 11 another embodiment of the appliance 10 is depicted. In these figures, the appliance 10 is the same as described above and depicted in the FIGS. 1-8, except as noted below. Thus, like reference numbers will be used for the same features.

The appliance 10 is provided with the polymer layer 212 as described above. In addition, the appliance 10 is provided with a border 220 along at least a section of the perimeter 42.

The border 220 may be separately formed from the polymer layer 212 and then separately attached to it so as to be integral, unitary and one-piece with the polymer layer 212 or the border 220 may be initially integrally formed and thus unitary and one-piece with the polymer layer 212. The border 220 is preferably constructed of the same material as the polymer layer 212, or it may be a different material.

In the depicted embodiment, the border 220 extends from the first side cusp 28 forward about the perimeter 42 of the appliance 10 to the forward cusp 16. The border 10 extends about the perimeter 42 from the forward cusp 16 to the second side cusp 32. The border 220 has a complementary shape to the perimeter 42. Preferably, the border 220 extends continuously without interruption along the perimeter 42. While the border 220 is described and depicted as extending continuously from the first side cusp 28 to the second side cusp 32, it is possible that the border 220 may be in sections that may or may not be connected to one another.

The border 220 may have a thickness that is greater than the combined thickness of the appliance 10 and the polymer layer 212. In other words, the border 220 may extend radially above and/or below the first planar and second planar sides 46, 48. It is also permissible for the border 220 to have the same combined thickness of the appliance 10 and the polymer layer 212 or less than the combined thickness.

The border 220 provides a protective, relatively soft material, along the border 220 as mentioned above. Such a border 220 has been found to be advantageous as it functions to protect and further reduce effects of impacts that drive the appliance 10, such as the perimeter of the appliance 10, into the soft tissues, such as the lips and gums, of the user. More particularly, it has been found that the border 220 reduces, or prevents, the relatively hard perimeter edge of the appliance 10 from being driven into the soft tissues of the user.

Figure 12:
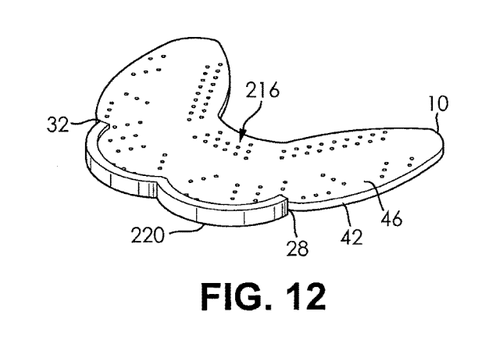
FIG. 12 depicts a perspective view of another embodiment of the mouth guard.
Figure 13:
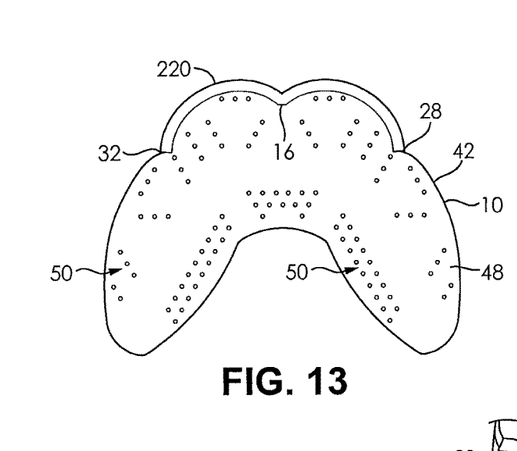
FIG. 13 depicts a bottom view of the mouth guard of FIG. 12.
Figure 14:
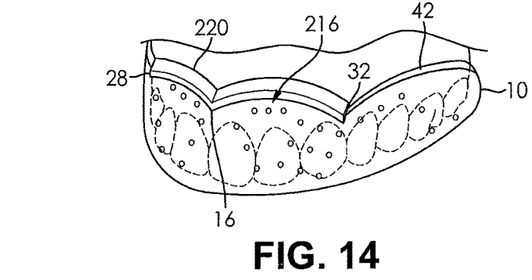
FIG. 14 depicts a perspective view of the mouth guard of FIG. 12 on the dentition of a user.

Turning now to FIGS. 12, 13 and 14 another embodiment of the appliance 10 is depicted. In these figures, the appliance 10 is the same as described above and depicted in the FIGS. 1-8, except as noted below. Thus, like reference numbers will be used for the same features.

In this embodiment, the appliance 10 is not provided with a polymer layer 212. Instead, the appliance 10 is provided with a border 220 as described above and depicted in FIGS. 9, 10 and 11.

Figure 15:
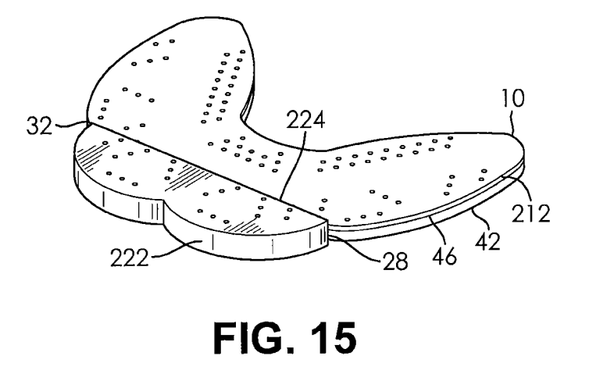
FIG. 15 depicts a perspective view of another embodiment of the mouth guard.
Figure 16:
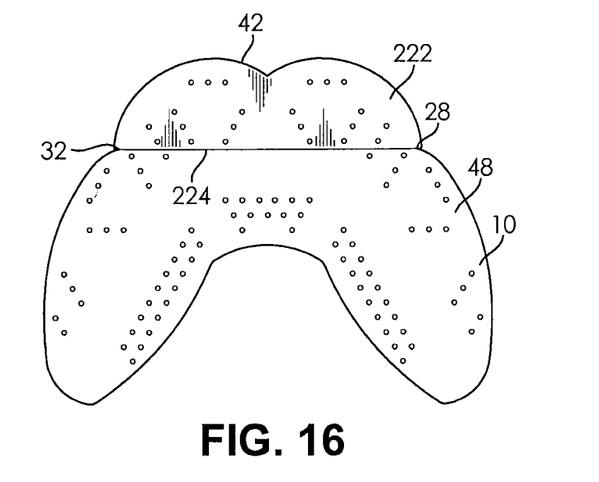
FIG. 16 depicts a bottom view of the mouth guard of FIG. 15.
Figure 17:
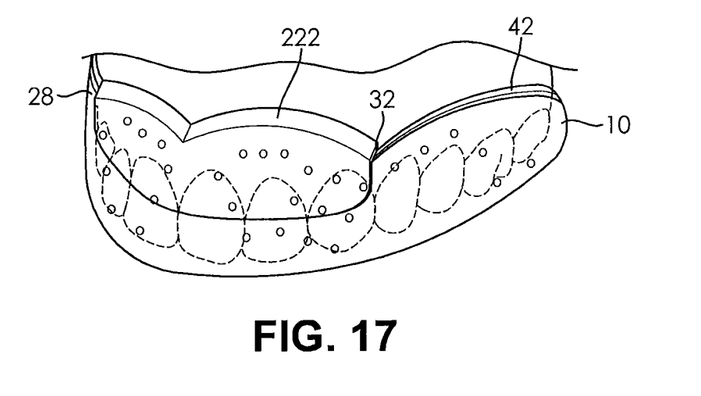
FIG. 17 depicts a perspective view of the mouth guard of FIG. 15 on the dentition of a user.

Turning now to FIGS. 15, 16 and 17 another embodiment of the appliance 10 is depicted. The polymer layer 212 is provided as described above and depicted in FIGS. 6, 7 and 8. In addition, a coating 222 is located over a portion of the polymer layer 212 and the appliance 10. As shown in FIGS. 15-17, the coating 222 is located over a portion of the polymer layer 212 on the first planar side 46 and a portion of the second planar side 48, which does not have the polymer layer 212.

The coating 222 preferably extends continuously without interruption from the first side cusp 28 and the second side cusp 32 forward on the appliance 10 to the forward cusp 16. The coating 222 has a complementary shape to the perimeter 42 of the appliance 10. Preferably, the coating 222 extends beyond the perimeter 42 at a constant thickness. The coating 222 terminates at a planar line 224 extending from the first side cusp 28 to the second side cusp 21. The coating 222 has a constant thickness.

The coating 222 has openings 226 corresponding to at least one of the sets of open spaces 50 in the appliance 10. Preferably, the coating 222 has openings corresponding to all of the sets of open spaces in the appliance 10 that the coating 222 overlaps.

The coating 222 thickness that extends beyond the perimeter 42 and the coating 222 over the polymer layer 212 provides a protective, relatively soft material. The coating 222 has been found to be advantageous as it functions to protect and further reduce effects of impacts that drive the appliance 10, such as the perimeter 42 of the appliance 10, into the soft tissues, such as the lips and gums, of the user. More particularly, it has been found that the coating 222 reduces, or prevents, the relatively hard appliance 10 from being driven into the soft tissues of the user.

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed is:

1. A mouth guard, comprising:
   a bite line separating an outer portion and an inner portion, said bite line extending through a line of symmetry of said guard, said line of symmetry dividing guard into a first half and a second half;
   a first set of open spaces and a second set of open spaces in said first half outer portion, wherein said first set of open spaces and said second set of open spaces are each comprised of three arrays of open spaces, wherein each array is comprised of three open spaces, wherein the arrays are arranged in a triangular pattern, wherein the triangular patterns of the arrays are not the same, wherein said first set of open spaces is located in a first front flap of the guard, and the second set of open spaces is located in a first outer side flap of the guard; and
   a third set of open spaces and a fourth set of open spaces in said second half outer portion, wherein said third set of open spaces and said fourth set of open spaces are each comprised of three arrays of open spaces, wherein each array is comprised of three open spaces, wherein the arrays are arranged in a triangular pattern, wherein the triangular patterns of the arrays are not the same, wherein said third set of open spaces is located in a second front flap of the guard, and the fourth set of open spaces is located in a second outer side flap of the guard.

2. The mouth guard of claim 1, wherein an imaginary line extending through the center of the second array of the first set of open spaces and an imaginary line extending through the center of the third array of the first set of open spaces intersect at a first point in the first half of the guard, and an imaginary line extending through the center of the second array of the second set of open spaces and an imaginary line extending through the center of the third array of the second set of open spaces intersect at a second point in the first half of the guard, where the first and the second points are different.

3. The mouth guard of claim 2, wherein an imaginary line extending through the center of the second array of the third set of open spaces and an imaginary line extending through the center of the third array of the third set of open spaces intersect at a third point in the second half of the guard, and an imaginary line extending through the center of the second array of the fourth set of open spaces and an imaginary line extending through the center of the third array of the fourth set of open spaces intersect at a fourth point in the second half of the guard, where the third and the fourth points are different.

4. The mouth guard of claim 1, wherein a fifth set of open spaces is located between the first set of open spaces and the second set of open spaces, wherein the fifth set of open spaces comprises an array of three open spaces, wherein said fifth set of open spaces is parallel an array in said first set of open spaces and an array in said second set of open spaces.

5. The mouth guard of claim 4, wherein a seventh and an eighth set of open spaces in said first half are parallel the fifth set of open spaces.

6. The mouth guard of claim 1, wherein a sixth set of open spaces is located between the third set of open spaces and the fourth set of open spaces, wherein the sixth set of open spaces comprises an array of three open spaces, wherein said sixth set of open spaces is parallel an array in said third set of open spaces and an array in said fourth set of open spaces.

7. The mouth guard of claim 6, wherein a ninth and a tenth set of open spaces in said second half are parallel said sixth set of open spaces.

8. The mouth guard of claim 1, wherein an imaginary line extending through the centers of one array of open spaces in the first set of open spaces and an imaginary line extending through the centers of one array of open spaces in the third set of open spaces intersect at a point outside of a perimeter of the guard directly out from said forward cusp.

9. The mouth guard of claim 1, wherein said first set of open spaces and said third set of open spaces are mirror images of one another, and said second set of open spaces and said fourth set of open spaces are mirror images of one another.

10. A mouth guard, comprising:
    a flat sheet having a first planar side and a second planar side parallel to said first planar side;
    a perimeter bounding said two sides and defining at least two cusps that extend inwardly into said flat sheet;
    a bite line that separates an inner portion from an outer portion, said bite line extending across a first half and a second half of the sheet;
    a first unperforated area located between a rearmost portion of the first half of the sheet and a first set of open spaces;
    a second unperforated area located between the first set of open spaces and a second set of open spaces on the outer portion of the first half;
    a third unperforated area located between the second set of open spaces and a third set open spaces on the outer portion of the first half;
    a fourth set of open spaces located between the third set of open spaces and a fifth set of open spaces on the outer portion of the first half;
    a fourth unperforated area located between the fifth set of open spaces and a sixth set of open spaces, said fourth unperforated area on the outer portion and spanning the first half and the second half;
    a seventh set of open spaces located between the sixth set of open spaces and an eighth set of open spaces on the outer portion of the second half;
    a fifth unperforated area located between the eighth set of open spaces and a ninth set of open spaces on the outer portion of the second half;
    a sixth unperforated area located between the ninth set of open spaces and a tenth set of open spaces;
    a seventh unperforated area located between a rearmost portion of the second half of the sheet and the tenth set of open spaces;
    wherein the third, fifth, sixth, and eighth sets of open spaces each comprise three arrays of three open spaces where the three arrays are arranged in a triangular pattern.

11. A mouth guard, comprising:
    a bite line separating an outer portion and an inner portion, said bite line extending through a line of symmetry of said guard, said line of symmetry dividing guard into a first half and a second half;
    a first set of open spaces and a second set of open spaces in said first half outer portion, wherein said first set of open spaces and said second set of open spaces are each comprised of three arrays of open spaces, wherein the arrays are arranged in a triangular pattern, wherein an imaginary line extending through one of said arrays of said first set of open spaces and an imaginary line extending through another of said arrays of said first set of open spaces meet at a point in the outer portion, wherein an imaginary line extending through one of said arrays of said second set of open spaces and an imaginary line extending through another of said arrays of said second set of open spaces meet at a point in the inner portion;
a third set of open spaces and a fourth set of open spaces in said second half outer portion, wherein said third set of open spaces and said fourth set of open spaces are each comprised of three arrays of open spaces, wherein the arrays are arranged in a triangular pattern, wherein an imaginary line extending through one of said arrays of said third set of open spaces and an imaginary line extending through another of said arrays of said third set of open spaces meet at a point in the outer portion, wherein an imaginary line extending through one of said arrays of said fourth set of open spaces and an imaginary line extending through another of said arrays of said fourth set of open spaces meet at a point in the inner portion.

12. A mouth guard, comprising:
a flat sheet having a first planar side and a second planar side parallel to said first planar side;
a perimeter bounding said two sides and defining at least two cusps that extend inwardly into said flat sheet;
a bite line that separates an inner portion from an outer portion, said bite line extending across a first half and a second half of the sheet;
a first set of open spaces and a second set of open spaces in said first half outer portion, wherein said first set of open spaces and said second set of open spaces are each comprised of three arrays of open spaces, wherein the arrays are arranged in a triangular pattern, wherein an imaginary line extending through one of said arrays of said first set of open spaces and an imaginary line extending through another of said arrays of said first set of open spaces meet at a point in the outer portion, wherein an imaginary line extending through one of said arrays of said second set of open spaces and an imaginary line extending through another of said arrays of said second set of open spaces meet at a point in the inner portion;
a third set of open spaces and a fourth set of open spaces in said second half outer portion, wherein said third set of open spaces and said fourth set of open spaces are each comprised of three arrays of open spaces, wherein the arrays are arranged in a triangular pattern, wherein an imaginary line extending through one of said arrays of said third set of open spaces and an imaginary line extending through another of said arrays of said third set of open spaces meet at a point in the outer portion, wherein an imaginary line extending through one of said arrays of said fourth set of open spaces and an imaginary line extending through another of said arrays of said fourth set of open spaces meet at a point in the inner portion; and
a polymer layer on said first planar side, wherein said polymer layer extends continuously across said first planar side to be coplanar with said perimeter except said polymer layer has openings corresponding to at least one of said sets of open spaces.

13. The mouth guard of claim 12, wherein said polymer layer has a constant thickness across said first planer side except for said at least one of said sets of open spaces.

14. The mouth guard of claim 12, wherein said polymer layer is a different material than the flat sheet.

15. The mouth guard of claim 12, wherein said polymer layer has openings corresponding to all of said sets of open spaces in said flat sheet.

16. The mouth guard of claim 14, wherein said polymer layer is ethylene-vinyl acetate and flat sheet is a polycaprolactone thermoplastic.

17. The mouth guard of claim 12, wherein a border of polymer is added to a section of the perimeter, wherein said border has a complementary shape to said perimeter, wherein said border extends from a first side cusp across a forward cusp to a second side cusp.

18. The mouth guard of claim 17, wherein said border has a thickness that is greater than the thickness of said flat sheet.

19. The mouth guard of claim 12, wherein a coating is located over a portion of said polymer layer on said first planar side, and said coating is located over a portion of said second planar side, wherein said coating has openings corresponding to at least one of said sets of open spaces in said flat sheet.

20. The mouth guard of claim 19, wherein said coating extends from a first side cusp and a second side cusp forward to a forward cusp to have a complementary shape to at least a portion of the perimeter.

* * * * *